(12) United States Patent
Park et al.

(10) Patent No.: US 11,241,242 B2
(45) Date of Patent: Feb. 8, 2022

(54) MICRONEEDLE ARRAY FOR ADMINISTERING VARIOUS TYPES OF DRUGS, MICRONEEDLE STRUCTURE INCLUDING MICRONEEDLE ARRAY, METHOD OF FABRICATING MICRONEEDLE ARRAY, AND METHOD OF FABRICATING MICRONEEDLE STRUCTURE

(71) Applicant: QuadMedicine, Seongnam-si (KR)

(72) Inventors: Jung Hwan Park, Seongnam-si (KR); Hye Rin Jeong, Seongnam-si (KR); Jee Hyun Park, Seoul (KR); Dae Seong Kim, Seosan-si (KR)

(73) Assignee: QuadMedicine, Seongnam-si (KR)

( * ) Notice: Subject to any disclaimer, the term of this patent is extended or adjusted under 35 U.S.C. 154(b) by 261 days.

(21) Appl. No.: 16/523,037

(22) Filed: Jul. 26, 2019

(65) Prior Publication Data
US 2020/0029981 A1 Jan. 30, 2020

(30) Foreign Application Priority Data
Jul. 27, 2018 (KR) ........................ 10-2018-0087947

(51) Int. Cl.
*A61B 17/20* (2006.01)
*A61M 37/00* (2006.01)
*A61K 9/00* (2006.01)

(52) U.S. Cl.
CPC .......... *A61B 17/205* (2013.01); *A61K 9/0021* (2013.01); *A61M 37/0015* (2013.01);
(Continued)

(58) Field of Classification Search
CPC ............ A61B 17/205; A61M 37/0015; A61M 2037/0053; A61M 2037/0023;
(Continued)

(56) References Cited

U.S. PATENT DOCUMENTS

2015/0112250 A1\* 4/2015 Kwon ............... A61M 37/0015
604/46
2016/0015952 A1\* 1/2016 Omachi ............... A61K 9/0021
604/46
2017/0304603 A1\* 10/2017 Kato .................... A61B 17/205

FOREIGN PATENT DOCUMENTS

JP 2011-506023 A 3/2011
JP 5285943 B2 9/2013

OTHER PUBLICATIONS

Communication dated Feb. 27, 2020, issued by the Korean Patent Office in counterpart Korean Patent Application No. 10-2018-0087947.
(Continued)

*Primary Examiner* — Amber R Stiles
(74) *Attorney, Agent, or Firm* — Sughrue Mion, PLLC (57) ABSTRACT

A microneedle array includes a plurality of microneedles of which surfaces are coated with a liquid drug and a base for supporting the microneedles in which the microneedles are divided into two or more areas, and the surfaces of microneedles disposed in each of the divided areas are coated with different liquid drugs, and the ingredient of a liquid drug coated on microneedles disposed in one of the divided areas is different from the ingredients of liquid drugs coated on microneedles disposed in the remainder of the divided areas.

14 Claims, 10 Drawing Sheets

(52) U.S. Cl.
CPC .............. *A61M 2037/0023* (2013.01); *A61M 2037/0053* (2013.01); *A61M 2202/30* (2013.01)

(58) Field of Classification Search
CPC ...... A61M 2202/30; A61M 2037/0046; A61K 9/0021; B05C 3/02
See application file for complete search history.

(56) References Cited

OTHER PUBLICATIONS

Song Li et al., "Individually coated microneedles for co-delivery of multiple compounds with different properties", Drug Delivery and Translational Research, Jun. 12, 2018.

* cited by examiner

MICRONEEDLE ARRAY FOR ADMINISTERING VARIOUS TYPES OF DRUGS, MICRONEEDLE STRUCTURE INCLUDING MICRONEEDLE ARRAY, METHOD OF FABRICATING MICRONEEDLE ARRAY, AND METHOD OF FABRICATING MICRONEEDLE STRUCTURE

CROSS-REFERENCE TO RELATED APPLICATION

This application claims priority to Korean Patent Application No. 10-2018-0087947, filed on Jul. 27, 2018 in the Korean Intellectual Property Office, the disclosure of which is incorporated herein by reference.

BACKGROUND OF THE DISCLOSURE

Field of the Disclosure

The present disclosure relates to a microneedle array for administering various kinds of drugs, a microneedle structure including the microneedle array, a method of fabricating the microneedle array, and a method of fabricating the microneedle structure. According to the present disclosure, a microneedle array is divided into several areas, and microneedles disposed in each area are separately coated with different liquid drugs. In this case, the ingredient of a liquid drug coated on microneedles disposed in one of the areas is different from the ingredients of liquid drugs coated on microneedles disposed in the remainder of the areas. Accordingly, various kinds of vaccines or multivalent antigens may be administered through one microneedle structure.

Description of the Related Art

In general, in transdermal drug delivery methods, the kinds of drugs are limited depending on the molecular weights of the drugs. To overcome this limitation, various active transdermal drug delivery methods have recently been proposed. Thereamong, a microneedle method of delivering a drug directly to the skin layer through the keratin layer of epidermis is attracting considerable attention. Microneedles used in the microneedle method are divided into four types as coating microneedles, solid microneedles, meltable microneedles, and hollow microneedles.

Mixed vaccines are classified as a mixed vaccine consisting of antigens for various subtypes of one disease, such as influenza vaccines, polio vaccines, and pneumococcal vaccines, and a mixed vaccine consisting of antigens for different diseases, such as DTaP vaccine and MMR vaccine. Since such a mixed vaccine contains one or more components, the components may interact and response to each component may be reduced or increased, as compared to a vaccine containing one component.

For this reason, development of mixed vaccines is a major problem, and many unexpected problems may arise when using mixed vaccines. When different types of antigens are mixed, quality, stability, safety, clinical tolerance, and efficacy/immunogenicity should be considered. In addition, early in development of a mixed vaccine, studies should be conducted to determine the stability and formulation of each component of the mixed vaccine containing preservatives, additives, and conjugates and compatibility between the components. Thus, there are restrictions on the development and use of mixed vaccines. On the other hand, a method of administering a single antigen has a problem that the number of times of inoculation is increased.

However, in the case of conventional microneedles, a multivalent antigen is distributed in one array, thereby increasing the number of administration. Alternatively, a vaccine containing multivalent antigens is distributed in one array, such that the efficacy of each component may be reduced.

SUMMARY OF THE DISCLOSURE

Therefore, the present disclosure has been made in view of the above problems, and it is an object of the present disclosure to provide a microneedle array for administering various drugs, a microneedle structure including the microneedle array, a method of fabricating the microneedle array, and a method of fabricating the microneedle structure. According to the present disclosure, microneedles disposed in a microneedle structure are divided into a plurality of areas, and the microneedles disposed in each area are separately coated with different liquid drugs. In this case, the ingredient of a liquid drug coated on microneedles disposed in one of the areas is different from the ingredients of liquid drugs coated on microneedles disposed in the remainder of the areas. Accordingly, various vaccines or multivalent antigens may be administered through one microneedle structure at one time, thereby improving convenience. In addition, the efficacy of each ingredient contained in the liquid drugs may be effectively delivered.

It is another object of the present disclosure to provide a microneedle array for administering various drugs, a microneedle structure including the microneedle array, a method of fabricating the microneedle array, and a method of fabricating the microneedle structure. According to the present disclosure, existing fabrication processes may be used without additional equipment, thereby improving fabrication efficiency and economic efficiency.

In accordance with the present disclosure, the above and other objects can be accomplished by the provision of a microneedle array including a plurality of microneedles, the surfaces of which are coated with a liquid drug and a base for supporting the microneedles, wherein the microneedles are divided into two or more areas, and the surfaces of microneedles disposed in each of the divided areas are coated with different liquid drugs, wherein the ingredient of a liquid drug coated on microneedles disposed in one of the divided areas is different from the ingredients of liquid drugs coated on microneedles disposed in a remainder of the divided areas.

According to one embodiment, the microneedles and the base may be integrally formed.

According to one embodiment, the areas that divide microneedles may be spaced apart from each other by a predetermined interval.

According to one embodiment, an interval between the areas may be formed wider than an interval between the microneedles.

According to one embodiment, one or more microneedles disposed in one of the areas may be coated with a liquid drug of an identical ingredient.

According to one embodiment, microneedles disposed in each of the areas may be coated with different monovalent antigens or vaccines, so that multivalent antigens or various vaccines may be provided by a single administration.

In accordance with an aspect of the present disclosure, the above and other objects can be accomplished by the provision of a microneedle structure including a plurality of microneedle arrays, some of the surfaces of which are coated with a liquid drug and a body for supporting the microneedle arrays, wherein the microneedle arrays are coupled to the body so that the microneedle arrays are divided into two or more areas, and the microneedle arrays are coated with different liquid drugs, wherein the ingredient of a liquid drug coated on at least one of the microneedle arrays is different from the ingredients of liquid drugs coated on the remainder of the microneedle arrays.

According to one embodiment, the microneedle array may include a plurality of microneedles, the surfaces of which are coated with a liquid drug of an identical ingredient, and a base for supporting the microneedles.

According to one embodiment, the areas defined by the microneedle arrays may be spaced apart from each other by a predetermined interval.

According to one embodiment, an interval between the areas may be formed wider than an interval between the microneedles.

According to one embodiment, microneedle arrays disposed in each of the areas may be coated with different monovalent antigens or vaccines, so that multivalent antigens or various vaccines may be provided by a single administration.

According to one embodiment, the microneedle arrays may be detachably coupled to the body.

According to one embodiment, a plurality of protrusion members protruding in one direction may be formed on the body, and coupling grooves may be formed in the surfaces of each of the microneedle arrays facing the body. In this case, the protrusion members may be inserted into the coupling grooves so that the microneedle arrays are coupled to the body.

According to one embodiment, a plurality of insertion grooves may be formed in the body, and each of the microneedle arrays may be inserted into the insertion grooves so that the microneedle arrays are coupled to the body.

According to one embodiment, a part of a side surface of the microneedle array may be cut to form a detachment groove.

In accordance with another aspect of the present disclosure, there is provided a method of fabricating a microneedle array including a step of forming a microneedle array including a plurality of microneedles and a base for supporting the microneedles and a step of dividing the microneedles into two or more areas and coating the surfaces of the microneedles disposed in each of the divided areas with different liquid drugs, wherein the ingredient of a liquid drug coated on the surfaces of microneedles disposed in one of the divided areas is different from the ingredients of liquid drugs coated on the surfaces of microneedles disposed in the remainder of the divided areas.

According to one embodiment, the step of coating may include a step of providing a container separated into at least two spaces and injecting different liquid drugs into each of the spaces, wherein the ingredient of a liquid drug injected into one of the spaces is different from the ingredients of liquid drugs injected into the remainder of the spaces, and a step of immersing the microneedle array in the container to coat the microneedles with different liquid drugs, wherein the ingredient of a liquid drug coated on at least one of the microneedles is different from the ingredients of liquid drugs coated on the remainder of the microneedles.

According to one embodiment, the surfaces of the microneedles may be coated with the liquid drug using a dip coating method.

In accordance with still another aspect of the present disclosure, there is provided a method of fabricating a microneedle structure including a step of forming at least two microneedle arrays, each including a plurality of microneedles and a base for supporting the microneedles; a step of coating microneedles disposed in each of the microneedle arrays with different liquid drugs, wherein the ingredient of a liquid drug coated on microneedles disposed in at least one of the microneedle arrays is different from the ingredients of liquid drugs coated on microneedles disposed in the remainder of the microneedle arrays; and a step of placing the microneedle arrays on one side of a body.

According to one embodiment, the step of coating includes a step of providing the same number of containers as the number of the microneedle arrays and injecting different liquid drugs into each of the containers, wherein the ingredient of a liquid drug injected into one of the containers is different from the ingredients of liquid drugs injected into the remainder of the containers, and a step of separately immersing the microneedle arrays in the corresponding container and independently coating the surfaces of microneedles disposed in each of the microneedle arrays with different liquid drugs, wherein the ingredient of a liquid drug coated on the surfaces of microneedles disposed in one of the microneedle arrays is different from the ingredients of liquid drugs coated on the surfaces of microneedles disposed in a remainder of the microneedle arrays.

According to one embodiment, the step of placing may include a step of coupling the microneedle arrays to the body by inserting coupling grooves formed in one side of each of the microneedle arrays into two or more protrusion members protruding from one side of the body.

According to one embodiment, the step of placing may include a step of coupling the microneedle arrays to the body by inserting the microneedle arrays into insertion grooves formed in one side of the body.

According to one embodiment, the surfaces of the microneedles may be coated with the liquid drug using a dip coating method.

BRIEF DESCRIPTION OF THE DRAWINGS

The above and other objects, features and other advantages of the present disclosure will be more clearly understood from the following detailed description taken in conjunction with the accompanying drawings, in which.

DETAILED DESCRIPTION OF THE DISCLOSURE

Hereinafter, a microneedle structure for administering various liquid drugs and a method of fabricating the same according to preferred embodiments will be described in detail with reference to the accompanying drawings. In this specification, the same or similar elements are designated by the same reference numerals. In addition, a detailed description of known functions and configurations incorporated herein will be omitted when it may make the subject matter of the present disclosure unclear. These embodiments are provided to more fully describe the present disclosure to those skilled in the art. Accordingly, the shapes and sizes of the elements in the drawings can be exaggerated for clarity.

Figure 1:
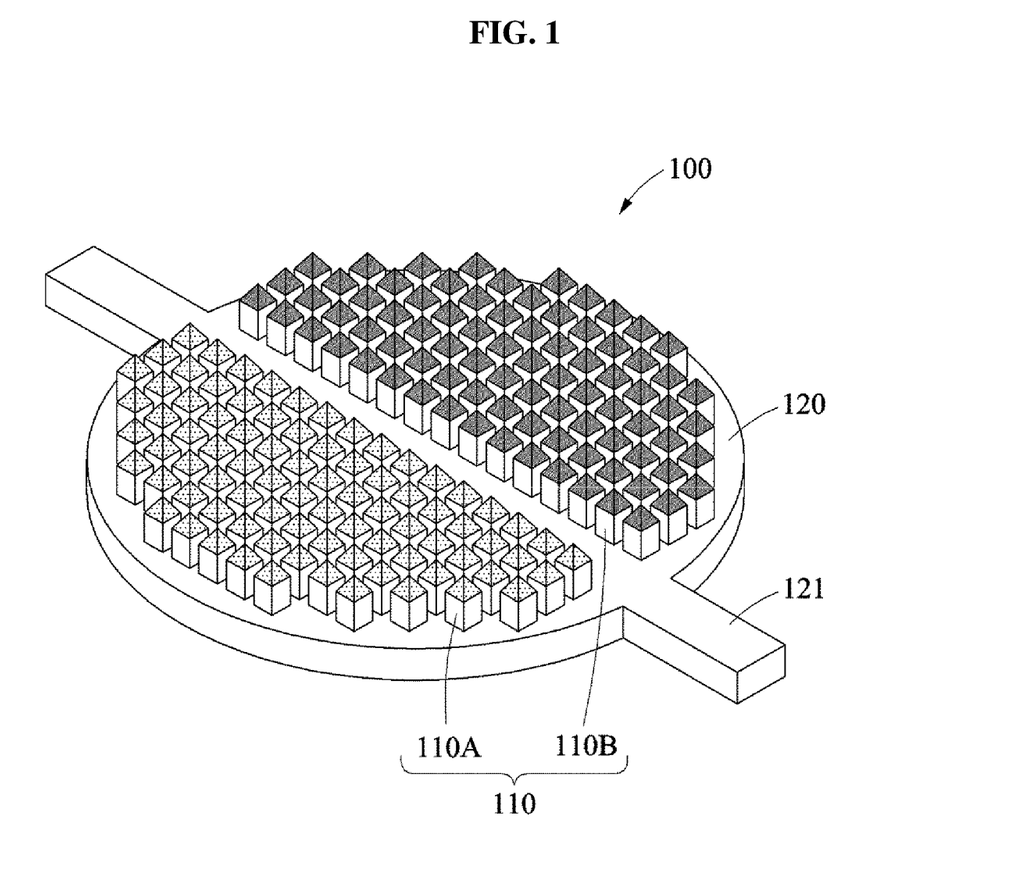
FIG. 1 is a perspective view of microneedle array according to one embodiment of the present disclosure.

FIG. 1 is a perspective view of microneedle array according to one embodiment of the present disclosure.

As shown in FIG. 1, a microneedle array 100 includes microneedles 110 and a base 120.

A plurality of microneedles 110 may be provided, and the surfaces thereof may be coated with a liquid drug. Specifically, the microneedles 110 penetrate into the skin, and the ends thereof may be formed to be sharp so as to easily penetrate the skin. In this embodiment, the microneedles 110 are formed in a quadrangular pyramid shape. However, the microneedles 110 may be implemented in various shapes such as a cone and a hexagonal pyramid.

The base 120 may be formed in a circular plate shape to support the microneedles 110. The base 120, which is a part of the body of the microneedle array 100, may be formed in close contact with the skin, and may be integrally formed with the microneedles 110.

At least one handle 121 may be formed on the side surface of the base 120. The handle 121 may be formed by protruding a part of the side surface of the base 120. That is, the handle 121 may be integrally formed with the base 120. As described above, when the handle 121 is formed on the base 120, grip may be easy, and usability may be improved.

In addition, the microneedles 110 may be divided into two or more areas, and the surfaces of the microneedles 110 disposed in each of the divided areas may be coated with different liquid drugs, wherein the ingredient of a liquid drug coated on the surfaces of the microneedles 110 disposed in one of the divided areas is different from the ingredients of liquid drugs coated on the surfaces of the microneedles 110 disposed in the remainder of the divided areas. That is, among the divided areas, the microneedles 110 disposed in the same area are coated with a liquid drug of an identical ingredient. In this case, the liquid drug may include at least one of an antigen, a vaccine, a hormone, an enzyme, a protein, and a synthetic medicine.

Since the microneedles 110 are divided into at least two regions, the microneedles 110 disposed in each area are coated with different monovalent antigens or vaccines, so that multivalent antigens or various vaccines may be supplied by a single administration.

For example, as shown in FIG. 1, when the microneedles 110 are divided into two areas, microneedles disposed on the left side in the drawing are referred to as first microneedles 110A, microneedles disposed on the right side are referred to as second microneedles 110B, and the ingredient of a liquid drug coated on the first microneedles 110A is different from that of a liquid drug coated on the second microneedles 110B. In this case, areas that divide the first microneedles 110A and the second microneedles 110B may be spaced apart from each other by a predetermined interval. The interval between these areas may be greater than the interval between the microneedles 110.

As described above, since multivalent antigens or various vaccines may be supplied by a single administration through the microneedle array 100, the number of administration of a liquid drug may be reduced, and the efficacy of each ingredient contained in the liquid drugs may be effectively delivered. Particularly, since a mixed vaccine contains a plurality of ingredients, there is a problem that the efficacy of each ingredient is reduced as compared with when each ingredient is administered alone. However, when the microneedles 110 are coated with liquid drugs of different ingredients as in the present disclosure, a plurality of liquid drugs may be effectively delivered by a single administration.

Figure 2:
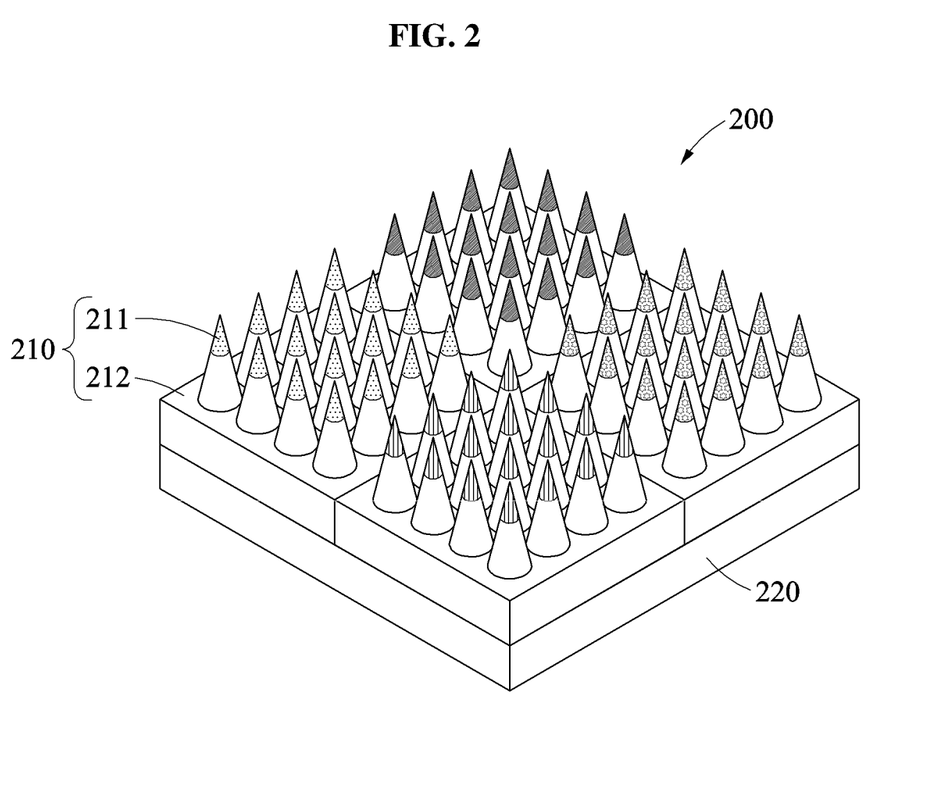
FIG. 2 is a perspective view of a microneedle structure according to one embodiment of the present disclosure.
Figure 3:
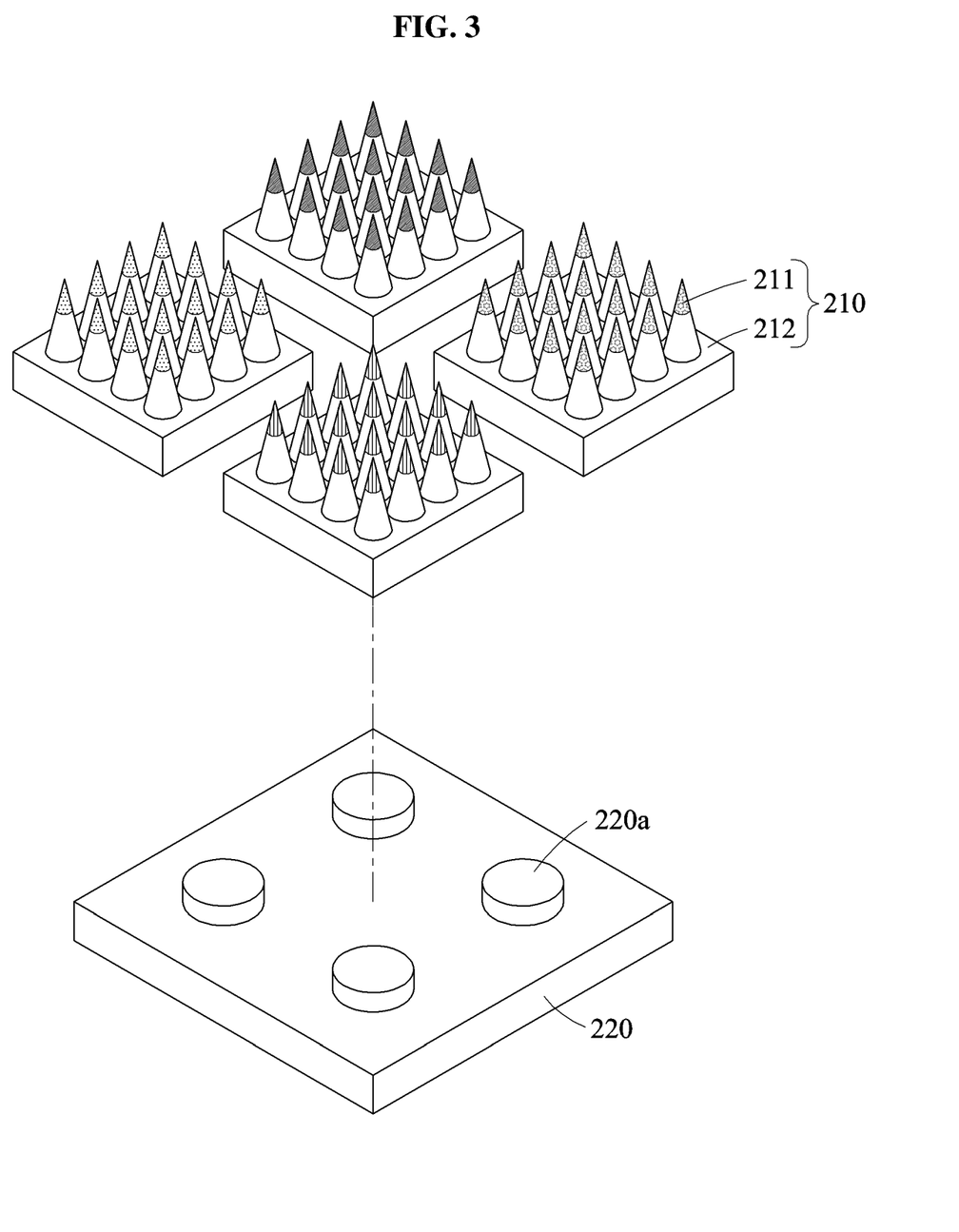
FIG. 3 is an exploded perspective view of the microneedle structure illustrated in FIG. 2.
Figure 4:
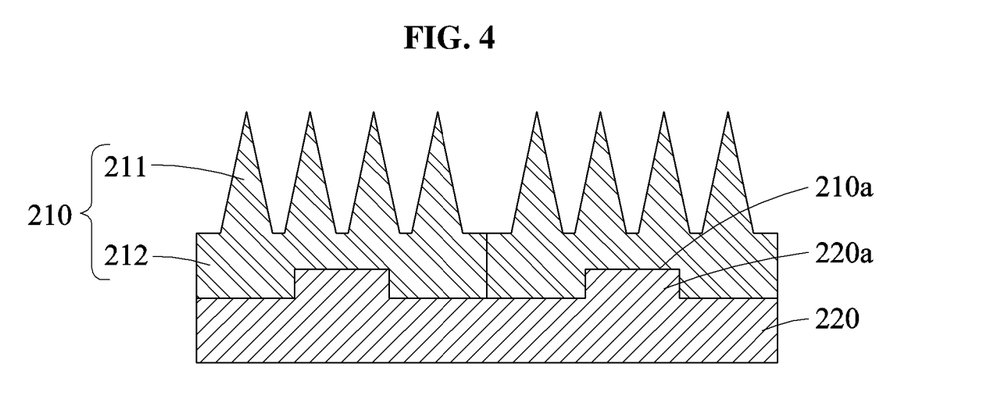
FIG. 4 is a cross-sectional view of the microneedle structure illustrated in FIG. 2.

FIG. 2 is a perspective view of a microneedle structure according to one embodiment of the present disclosure, FIG. 3 is an exploded perspective view of the microneedle structure illustrated in FIG. 2, and FIG. 4 is a cross-sectional view of the microneedle structure illustrated in FIG. 2.

As shown in FIGS. 2 to 4, a microneedle structure 200 includes microneedle arrays 210 and a body 220.

A plurality of the microneedle arrays 210 may be provided, and some of the surfaces of the microneedle arrays 210 may be coated with liquid drugs. Specifically, a plurality of microneedles 211 coated with a liquid drug and a base 212 for supporting the microneedles 211 may be formed on the surface of each of the microneedle arrays 210. In this case, the microneedles 211 and the base 212 may be integrally formed.

The body 220 may support the microneedle arrays 210. In this case, the microneedle arrays 210 may be coupled to the body 220 so that the microneedle arrays 210 are divided into two or more areas.

Areas defined by the microneedle arrays 210 may be spaced apart from each other by a predetermined interval. The interval between the areas is preferably greater than the interval between the microneedles 211.

In this embodiment, the body 220 is illustrated as a quadrangle, but may be embodied in various shapes such as a circle or a hexagon. In addition, although not shown, a handle may be formed on one side of the body 220 for ease of use.

In addition, the ingredient of a liquid drug coated on at least one of the microneedle arrays 210 may be different from the ingredients of liquid drugs coated on the remainder of the microneedle arrays 210. That is, since the microneedles 211 disposed in each area are coated with different monovalent antigens or vaccines, multivalent antigens or various vaccines may be supplied by a single administration. For example, as shown in FIG. 2, when four microneedle arrays 210 are provided, the microneedle structure 200 may be coated with four kinds of liquid drugs. That is, the number of liquid drug types is determined depending on the number of the microneedle arrays 210.

However, the number of liquid drug types provided in the microneedle structure 200 is not limited thereto, and the amount of the liquid drug provided in the microneedle structure 200 may be adjusted by appropriately adjusting the number of liquid drug types. That is, when four microneedle arrays 210 are provided, the microneedle structure 200 may be coated with three kinds of liquid drugs. For example, when increasing the dosage of a liquid drug containing ingredient A among liquid drugs, each containing ingredient A, B, or C, two microneedle arrays 210 are coated with the liquid drug containing ingredient A and other microneedle arrays 210 are respectively coated with the liquid drug containing ingredient B and the liquid drug containing ingredient C.

The microneedle arrays 210 may be detachably coupled to the body 220. For example, as shown in FIG. 4, the microneedle arrays 210 may be detachably coupled to the body 220 via a plurality of protrusion members 220a formed on the body 220 and coupling grooves 210a formed in each base 212. Specifically, the protrusion members 220a may be formed in each of the divided areas of the body 220 so as to protrude upward, and the coupling grooves 210a may be formed in a lower surface of each base 212, that is, a surface facing the body 220.

Specifically, when four microneedle arrays 210 are provided, the body 220 may be divided into four areas. The protrusion members 220a are formed in each area of the body 220, and the protrusion members 220a are inserted into the coupling grooves 210a formed in the bottom surface of each of the microneedle arrays 210. In this case, the microneedle arrays 210 and the body 220 may be formed using adhesive materials so that the protrusion members 220a and the coupling grooves 210a are coupled to each other, or the protrusion members 220a and the coupling grooves 210a may be coupled to each other in a force-fitting manner.

Since the microneedle arrays 210 are detachably coupled to the body 220, various kinds of liquid drugs may be provided in the body 220, and the kind of a liquid drug may be changed as needed, thereby increasing usability.

In addition, since the microneedle arrays 210 are detachably coupled to the body 220, the microneedle arrays 210 provided in the body 220 may be partially used. For example, as shown in FIG. 4, when the body 220 is divided into four areas and three kinds of liquid drugs are used, one of the microneedle arrays 210 may be separated and the remaining three microneedle arrays 210 may be used. Accordingly, the kind and content of a liquid drug may be appropriately adjusted and used.

Figure 5:
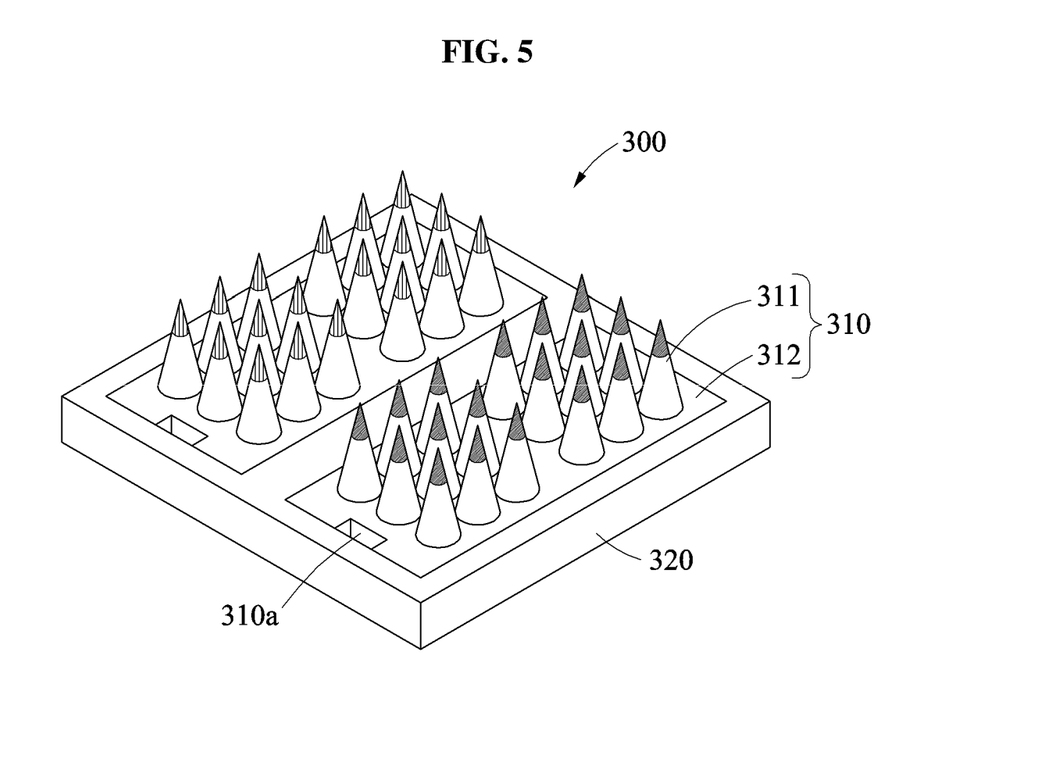
FIG. 5 is a perspective view of a microneedle structure according to another embodiment of the present disclosure.
Figure 6:
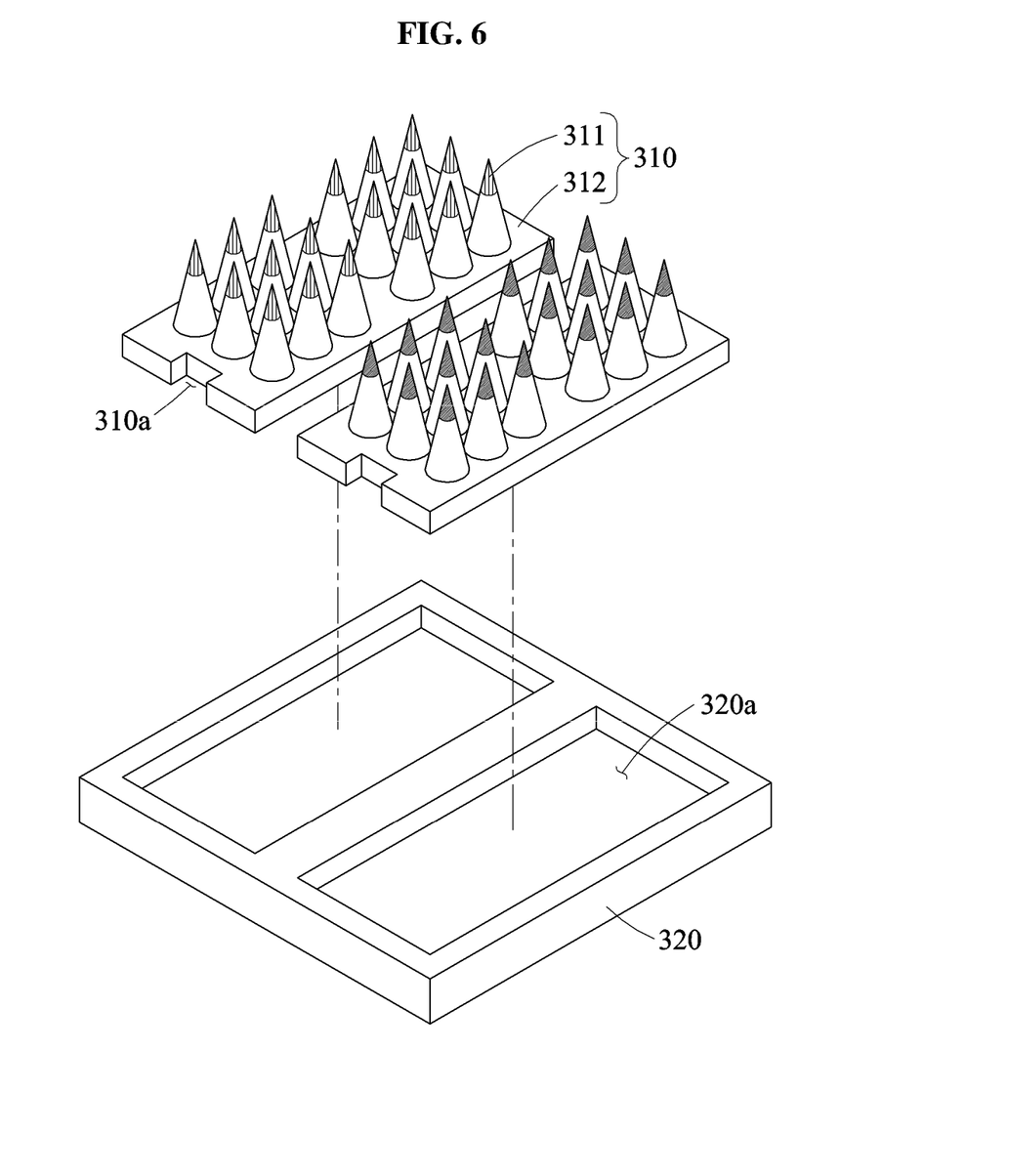
FIG. 6 is an exploded perspective view of the microneedle structure illustrated in FIG. 5.

FIG. 5 is a perspective view of a microneedle structure according to another embodiment of the present disclosure, and FIG. 6 is an exploded perspective view of the microneedle structure illustrated in FIG. 5. In this embodiment, differences from the above-described embodiment will be mainly described.

As shown in FIGS. 5 and 6, a microneedle structure 300 may include two or more microneedle arrays 310, wherein some of the surfaces of the microneedle arrays 310 is coated with a liquid drug, and a body 320 for supporting the microneedle arrays 310. Specifically, a plurality of microneedles 311 coated with a liquid drug and a base 312 for supporting the microneedles 311 may be formed on the surface of the microneedle arrays 310.

The surfaces of the microneedles 311 disposed in each of the microneedle arrays 310 may be coated with different liquid drugs, wherein the ingredient of a liquid drug coated on the surfaces of the microneedles 311 disposed in one of the microneedle arrays 310 may be different from the ingredients of liquid drugs coated on the surfaces of the microneedles 311 disposed in the remainder of the microneedle arrays 310. Accordingly, as shown in FIG. 5, when two microneedle arrays 310 are provided, the microneedle structure 300 may be coated with two kinds of liquid drugs.

The microneedle arrays 310 may be detachably coupled to the body 320. For example, as shown in FIG. 6, a plurality of insertion grooves 320a is formed in the divided areas of the body 320, and the base 312 of each of the microneedle arrays 310 is inserted into each of the insertion grooves 320a, so that the microneedle arrays 310 are coupled to the body 320. In this case, the insertion grooves 320a and the microneedle arrays 310 may be coupled to each other in a force-fitting manner or the body 320 and the microneedle arrays 310 may be formed using adhesive materials so that the body 320 and the microneedle arrays 310 are coupled to each other.

In addition, a detachment groove 310a may be formed in a side surface of the base 312. When the detachment groove 310a is formed in a side surface of the base 312, the microneedle arrays 310 may be more easily detached from the insertion grooves 320a.

As described above, since the microneedle structure includes microneedles coated with liquid drugs of different ingredients, multivalent antigens or various vaccines may be delivered by a single administration using one microneedle structure, thereby reducing the number of administration of liquid drugs and improving convenience.

In addition, in the case of a conventional method of administering a liquid drug containing various ingredients to a user, there is a problem that the efficacy of each ingredient is reduced due to interaction between the ingredients. According to the present disclosure, since microneedles are separately coated with liquid drugs of different ingredients, the efficacy of the ingredient contained in each liquid drug may be effectively delivered.

In addition, in the case of influenza vaccine, since the type of influenza that is prevalent changes every year, the previously prepared vaccine has to be discarded. However, when the microneedle structure of the present disclosure is used, a vaccine against influenza, which is prevalent every year, may be selected and mounted on the microneedle structure, thereby improving economic efficiency.

In addition, since a coating apparatus used in conventional non-divided microneedles can be used in the microneedles of the present disclosure without modification, additional equipment is not required and installation costs can be reduced.

Figure 7:
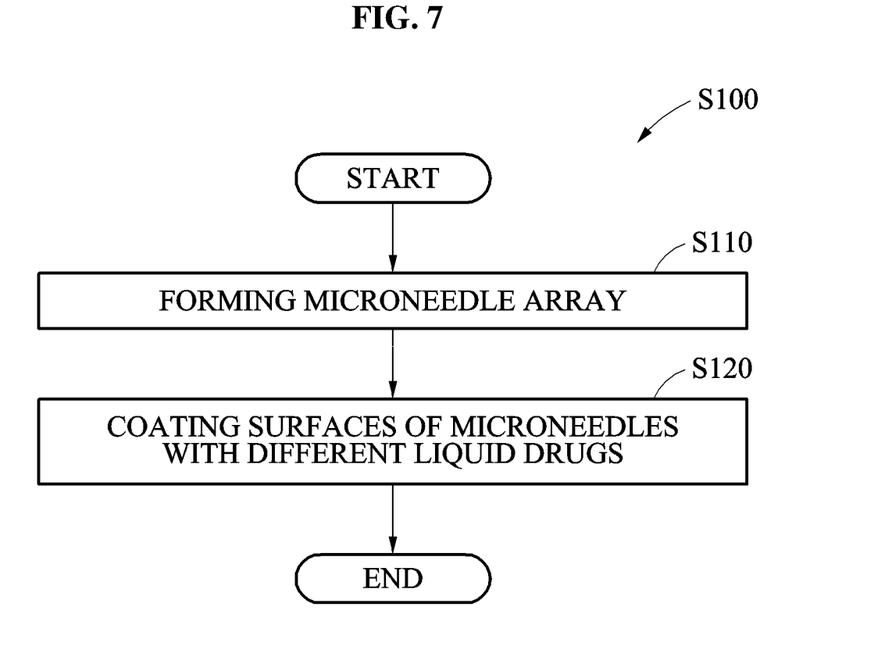
FIG. 7 is a block diagram showing a method of fabricating a microneedle array according to one embodiment of the present disclosure.
Figure 8:
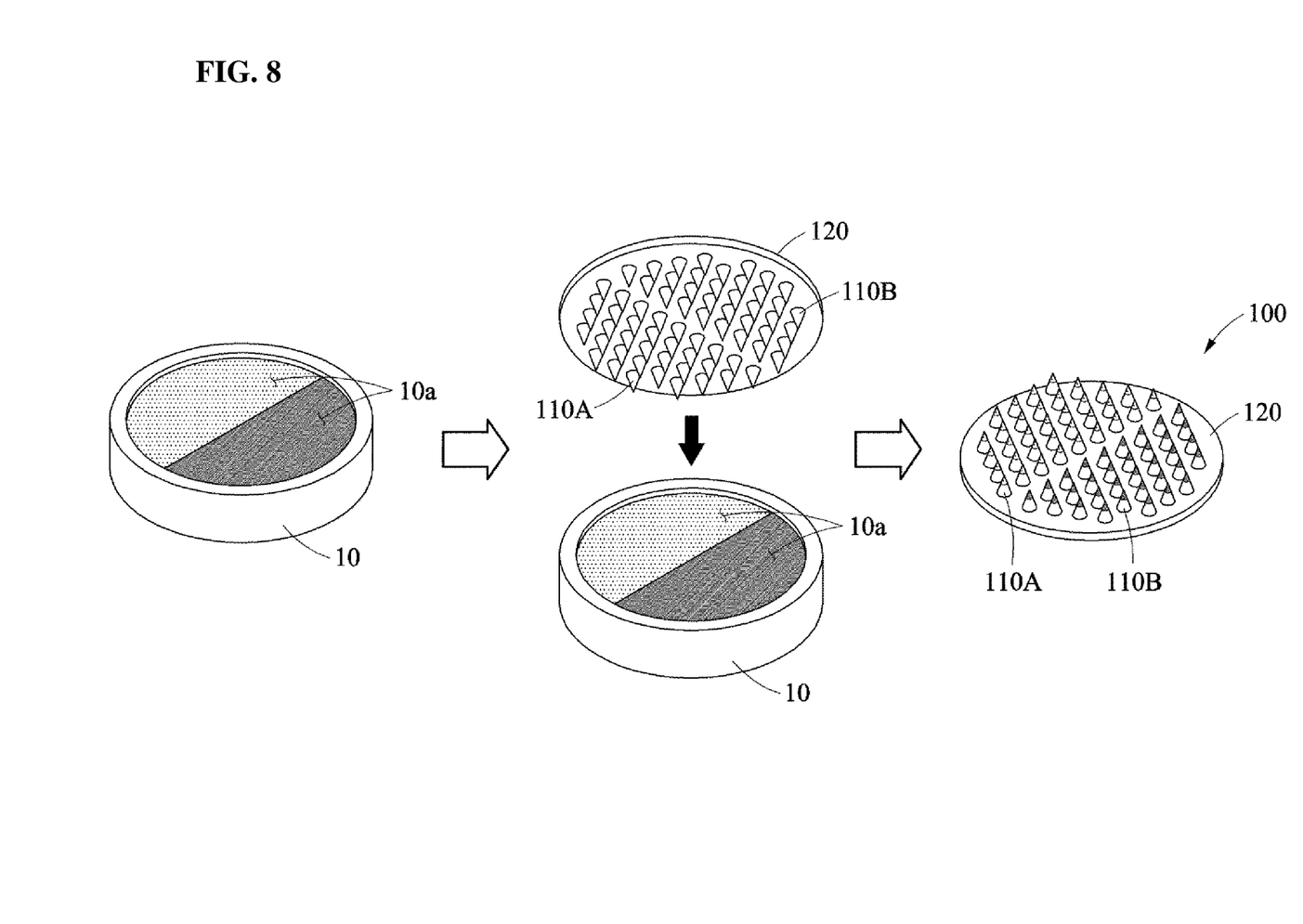
FIG. 8 includes drawings for explaining a process of fabricating the microneedle array illustrated in FIG. 7.

FIG. 7 is a block diagram showing a method of fabricating a microneedle array according to one embodiment of the present disclosure, and FIG. 8 includes drawings for explaining a process of fabricating the microneedle array illustrated in FIG. 7.

As shown in FIGS. 7 and 8, method S100 of fabricating a microneedle array may include step S110 of forming a microneedle array and step S120 of coating the surfaces of each set of microneedles with different liquid drugs, wherein the ingredient of a liquid drug coated on the surfaces of one set of microneedles is different from that of a liquid drug coated on the surfaces of the other set of microneedles.

In step S110, the microneedle array 100 may include the microneedles 110 and the base 120 for supporting the microneedles 110, and may be formed to have a predetermined shape. For example, a raw material may be injected into a mold (not shown) and molded and the mold may be removed to form the microneedle array 100.

In step S120, the microneedles 110 may be divided into two or more areas, and the surfaces of the microneedles 110 disposed in each of the divided areas are coated with different liquid drugs, wherein the ingredient of a liquid drug coated on the surfaces of the microneedles 110 disposed in one of the divided areas is different from the ingredients of liquid drugs coated on the surfaces of the microneedles 110 disposed in the remainder of the divided areas.

Specifically, as shown in FIG. 8, step S120 may include a step of providing a container 10 separated into at least two spaces 10a, a step of injecting different liquid drugs into each of the spaces 10a, wherein the ingredient of a liquid drug injected into one of the spaces 10a is different from the ingredients of liquid drugs injected into the remainder of the spaces 10a, and a step of immersing the microneedle array 100 in the container 10 to coat the microneedles 110 with liquid drugs of different ingredients, wherein the ingredient of a liquid drug coated on at least one of the microneedles 110 is different from the ingredients of liquid drugs coated on the remainder of the microneedles 110. When the microneedle array 100 is fabricated through this process, the microneedle array 100 may be separately coated with at least two liquid drugs.

The composition of a liquid drug to be coated on the microneedle array 100 may be selected from the following coating solutions 1 to 4. In this case, the ratio of an active ingredient to deionized water may vary depending on a subject to be administered, the kind of the active ingredient, and the like. In addition, the composition of the liquid drug is not limited thereto and may be variously implemented.

[Coating solution 1] active ingredient, deionized water (DW), 10% (w/w) carboxymethyl cellulose (CMC), 0.5% (w/w) Tween 80, 1% (w/w) trypan blue

[Coating solution 2] active ingredient, deionized water (DW), 10% (w/w) carboxymethyl cellulose (CMC), 0.5% (w/w) Tween 80, 1% (w/w) rhodamine B

[Coating solution 3] active ingredient, deionized water (DW), 10% (w/w) carboxymethyl cellulose (CMC), 0.5% (w/w) Tween 80, 1% (w/w) calcein

[Coating solution 4] active ingredient, deionized water (DW), 10% (w/w) carboxymethyl cellulose (CMC), 0.5% (w/w) Tween 80

In addition, the surfaces of the microneedles 110 may be coated with a liquid drug using a dip coating method. That is, the microneedles 110 may be immersed in a liquid drug, and after a certain period of time, the microneedles 110 may be taken out of the liquid drug and dried to coat the surfaces of the microneedles 110 with the liquid drug. When the surfaces of the microneedles 110 are coated with a liquid drug using the dip coating method, step S120 may further include a step of drying the microneedle array 100.

Figure 9:
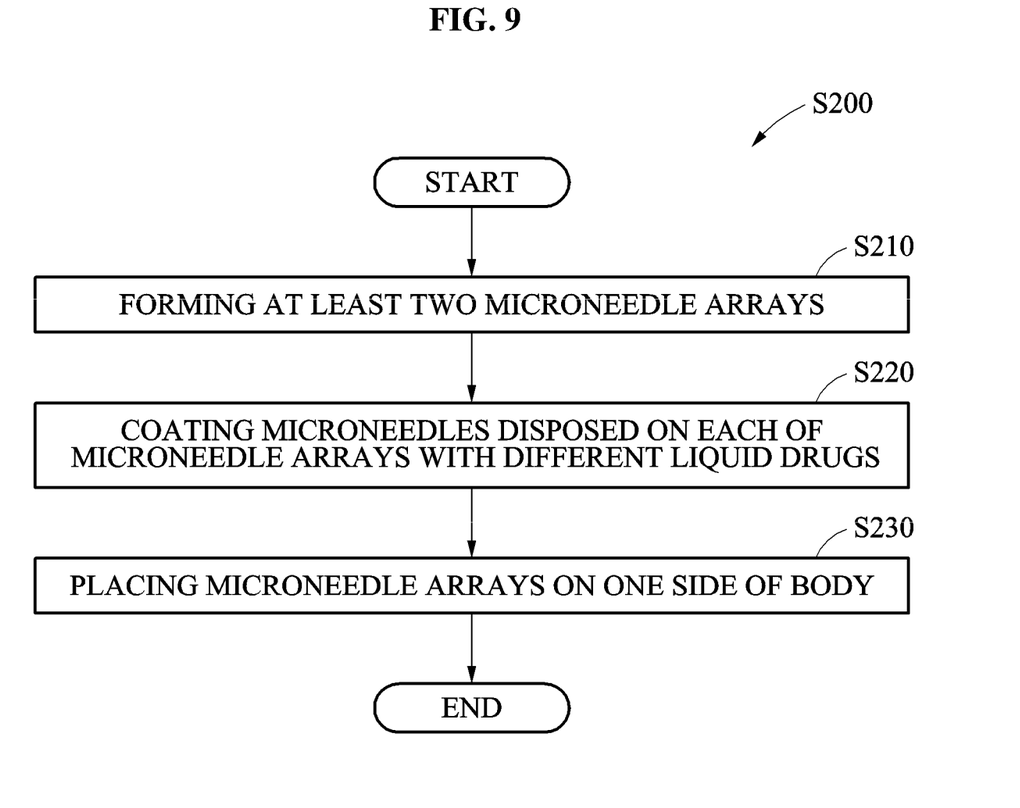
FIG. 9 is a block diagram showing a method of fabricating a microneedle structure according to one embodiment of the present disclosure.
Figure 10:
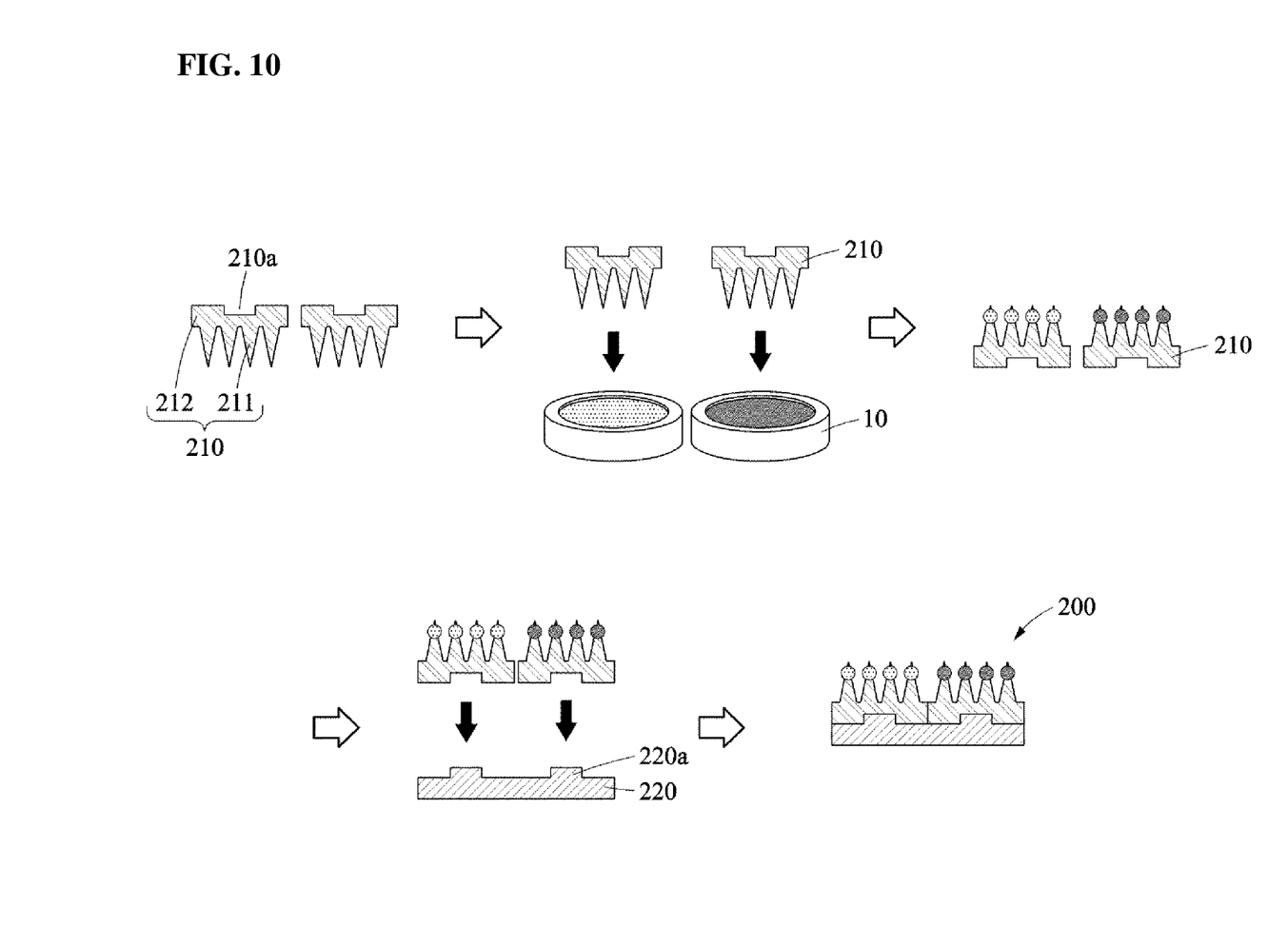
FIGS. 10 and 11 include drawings for explaining the method of fabricating a microneedle structure shown in FIG. 9.

FIG. 9 is a block diagram showing a method of fabricating a microneedle structure according to one embodiment of the present disclosure, and FIG. 10 includes drawings for explaining a process of fabricating the microneedle structure shown in FIG. 9. In this embodiment, differences from the above embodiment will be mainly described.

As shown in FIGS. 9 and 10, method S200 of fabricating a microneedle structure includes step S210 of forming at least two microneedle arrays, step S220 of coating microneedles disposed in each of the microneedle arrays with different liquid drugs, wherein the ingredient of a liquid drug coated on microneedles disposed in one of the microneedle arrays is different from the ingredients of liquid drugs coated on microneedles disposed in the remainder of the microneedle arrays, and step S230 of placing the microneedle arrays on one side of a body.

In step S210, at least two microneedle arrays 210 each including a plurality of microneedles 211 and the base 212 for supporting the microneedles 211 may be formed to have a predetermined shape.

In step S220, the ingredient of a liquid drug coated on the microneedles 211 disposed in at least one of the microneedle arrays 210 may be different from the ingredients of liquid drugs coated on the microneedles 211 disposed in the remainder of the microneedle arrays 210.

Specifically, as shown in FIG. 10, step S220 may include a step of providing the same number of containers 10 as the number of the microneedle arrays 210 and injecting different liquid drugs into each of the containers 10, wherein the ingredient of a liquid drug injected into one of the containers 10 is different from the ingredients of liquid drugs injected into the remainder of the containers 10 and a step of separately immersing the microneedle arrays 210 in the corresponding container 10 and independently coating the surfaces of the microneedles 211 disposed in each of the microneedle arrays 210 with different liquid drugs, wherein the ingredient of a liquid drug coated on the surfaces of the microneedles 211 disposed in one of the microneedle arrays 210 is different from the ingredients of liquid drugs coated on the surfaces of the microneedles 211 disposed in the remainder of the microneedle arrays 210.

When the microneedle structure 200 is fabricated through this process, one of the microneedle arrays 210 may be coated with a liquid drug containing a single ingredient, and each of the microneedle arrays 210 may be coated with liquid drugs with different ingredients. Accordingly, the microneedle structure 200 may be provided with a plurality of liquid drugs, each containing different ingredients.

In step S230, each of the microneedle arrays 210 is placed in one side of the body 220. For example, as shown in FIG. 10, step S230 may include a step of coupling the microneedle arrays 210 to the body 220 by inserting the protrusion members 220a protruding from one side of the body 220 into the coupling grooves 210a formed in one side of each of the microneedle arrays 210.

Figure 11:
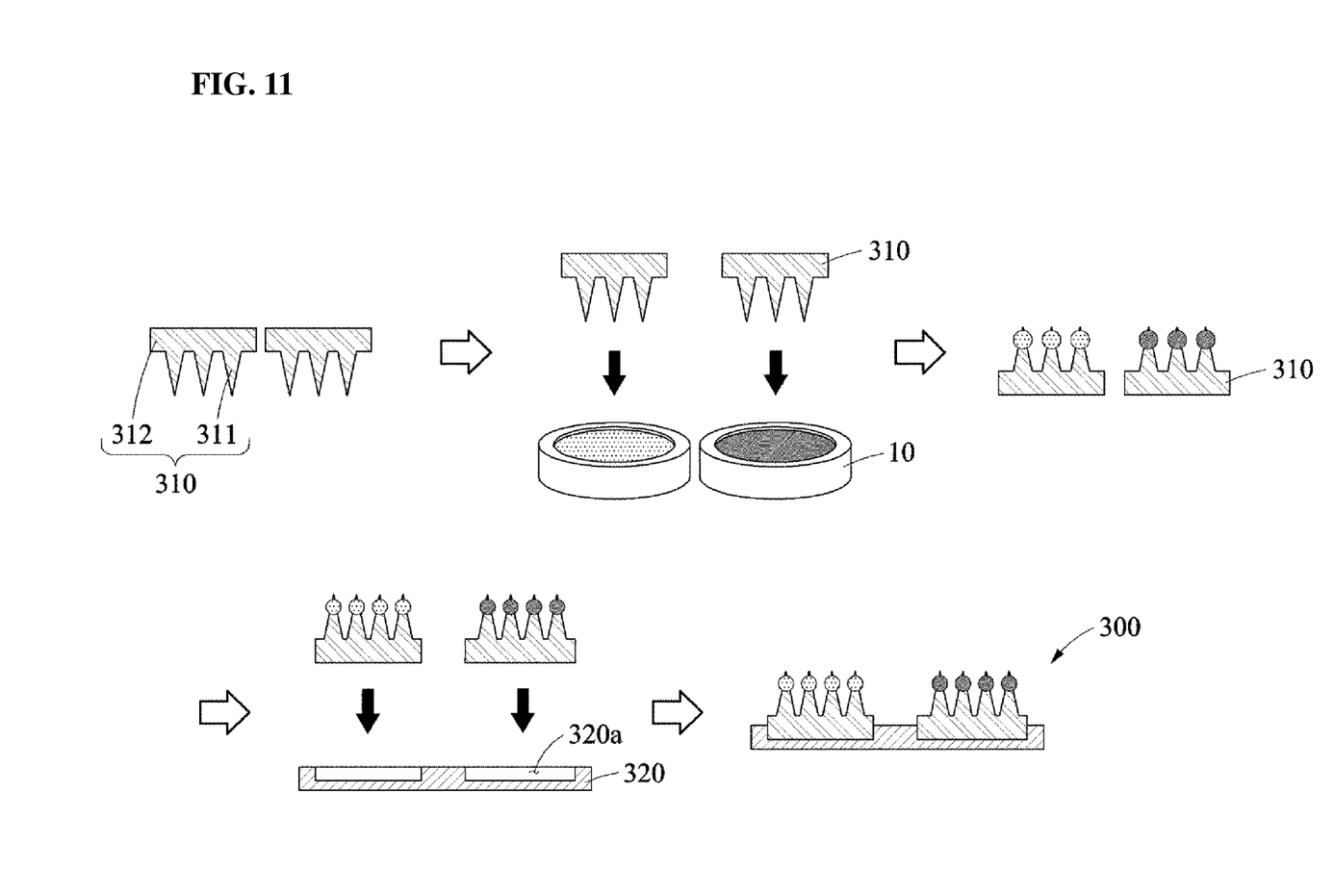

In addition, as shown in FIG. 11, step S230 may include a step of coupling the microneedle arrays 310 to the body 320 by inserting the microneedle arrays 310 into the insertion grooves 320a formed in one side of the body 320.

According to the present disclosure, since the microneedle structure includes microneedles coated with different liquid drugs with different ingredients, multivalent antigens or various vaccines can be delivered by a single administration using one microneedle structure, thereby reducing the number of administration of liquid drugs and improving convenience.

In addition, in the case of a conventional method of administering a liquid drug containing various ingredients to a user, there is a problem that the efficacy of each ingredient is reduced due to interaction between the ingredients. According to the present disclosure, since microneedles are separately coated with different liquid drugs, the efficacy of the ingredient contained in each liquid drug can be effectively delivered.

In addition, in the case of influenza vaccine, since the type of influenza that is prevalent changes every year, the previously prepared vaccine has to be discarded. However, when the microneedle structure of the present disclosure is used, a vaccine against influenza, which is prevalent every year, can be selected and mounted on the microneedle structure, thereby improving economic efficiency.

In addition, since a coating apparatus used in conventional non-divided microneedles can be used in the microneedles of the present disclosure without modification, additional equipment is not required and installation costs can be reduced.

Hereinafter, the present disclosure has been described in more detail with reference to the preferred examples. However, these examples are provided for illustrative purposes only and should not be construed as limiting the scope and spirit of the present disclosure. In addition, it will be apparent to those skilled in the art that various changes and modifications may be made without departing from the spirit and scope of the present disclosure, and such changes and modifications are also within the scope of the appended claims.

DESCRIPTION OF SYMBOLS

100: MICRONEEDLE ARRAY
110: MICRONEEDLES
120: BASE
121: HANDLES
200, 300: MICRONEEDLE STRUCTURE
210, 310: MICRONEEDLE ARRAYS
211, 311: MICRONEEDLES
212, 312: BASES
220, 320: BODY

What is claimed is:

1. A microneedle array, comprising:
a plurality of microneedles, wherein surfaces of the microneedles are coated with a liquid drug;
a base for supporting the microneedles; and
a body coupled to the base,
wherein the microneedles are divided into two or more areas, and surfaces of microneedles disposed in each of the divided areas are coated with different liquid drugs, wherein an ingredient of a liquid drug coated on microneedles disposed in one of the divided areas is different from ingredients of liquid drugs coated on microneedles disposed in a remainder of the divided areas,
wherein the base is divided into two or more base parts corresponding to the two or more areas,
wherein a plurality of protrusion members protruding in one direction are formed on the body, and coupling grooves are formed in surfaces of the two or more base parts facing the body, and
wherein the plurality of protrusion members are inserted into the coupling grooves so that the microneedle arrays are coupled to the body.

2. The microneedle array according to claim 1, wherein the microneedles and the base are integrally formed.

3. The microneedle array according to claim 1, wherein the areas that divide microneedles are spaced apart from each other by a predetermined interval.

4. The microneedle array according to claim 3, wherein the predetermined interval between the areas is formed wider than an interval between the microneedles.

5. The microneedle array according to claim 1, wherein one or more microneedles disposed in one of the areas are coated with a liquid drug of an identical ingredient.

6. The microneedle array according to claim 1, wherein microneedles disposed in each of the areas are coated with different monovalent antigens or different vaccines, so that multivalent antigens or the different vaccines are provided by a single administration.

7. A microneedle structure, comprising:
a plurality of microneedle arrays, wherein some surfaces of the microneedle arrays are coated with a liquid drug; and
a body for supporting the microneedle arrays,
wherein the microneedle arrays are coupled to the body so that the microneedle arrays are divided into two or more areas, and the microneedle arrays are coated with different liquid drugs, wherein an ingredient of a liquid drug coated on at least one of the microneedle arrays is different from ingredients of liquid drugs coated on a remainder of the microneedle arrays,
wherein a plurality of protrusion members protruding in one direction are formed on the body, and coupling grooves are formed in surfaces of the microneedle arrays facing the body, and
wherein the plurality of protrusion members are inserted into the coupling grooves so that the microneedle arrays are coupled to the body.

8. The microneedle structure according to claim 7, wherein each microneedle array of the microneedle arrays comprises a plurality of microneedles and a base for supporting the plurality of microneedles, and surfaces of the microneedles are coated with a liquid drug of an identical ingredient.

9. The microneedle structure according to claim 7, wherein the areas defined by the microneedle arrays are spaced apart from each other by a predetermined interval.

10. The microneedle structure according to claim 9, wherein the predetermined interval between the areas is formed wider than an interval between the microneedles.

11. The microneedle structure according to claim 7, wherein microneedle arrays disposed in each of the areas are coated with different monovalent antigens or different vaccines, so that multivalent antigens or the different vaccines are provided by a single administration.

12. The microneedle structure according to claim 7, wherein the microneedle arrays are detachably coupled to the body.

13. A microneedle structure, comprising:
a plurality of microneedle arrays, wherein some surfaces of the microneedle arrays are coated with a liquid drug; and
a body for supporting the microneedle arrays,
wherein the microneedle arrays are coupled to the body so that the microneedle arrays are divided into two or more areas, and the microneedle arrays are coated with different liquid drugs, wherein an ingredient of a liquid drug coated on at least one of the microneedle arrays is different from ingredients of liquid drugs coated on a remainder of the microneedle arrays,
wherein a plurality of insertion grooves are formed in the body, and each of the microneedle arrays is inserted into the insertion grooves so that the microneedle arrays are coupled to the body.

14. The microneedle structure according to claim 13, wherein a part of a side surface of each of the microneedle arrays is cut to form a detachment groove.

* * * * *